US010010367B2

(12) United States Patent
Chien et al.

(10) Patent No.: US 10,010,367 B2
(45) Date of Patent: Jul. 3, 2018

(54) STEERABLE ELECTROSURGICAL ELECTRODE

(71) Applicant: CoreBio Technologies Co., Ltd., Taoyuan (TW)

(72) Inventors: Chih-Hao Chien, Yilan County (TW); Chih-Hung Li, Taoyuan (TW)

(73) Assignee: COREBIO TECHNOLOGIES CO., LTD., Taoyuan (TW)

( * ) Notice: Subject to any disclaimer, the term of this patent is extended or adjusted under 35 U.S.C. 154(b) by 436 days.

(21) Appl. No.: 14/930,162

(22) Filed: Nov. 2, 2015

(65) Prior Publication Data
US 2017/0071658 A1 Mar. 16, 2017

(30) Foreign Application Priority Data

Sep. 11, 2015 (TW) .............................. 104130212 A (51) Int. Cl.
*A61B 18/14* (2006.01)
*A61B 17/00* (2006.01)
(Continued)

(52) U.S. Cl.
CPC ...... *A61B 18/1482* (2013.01); *A61B 18/1445* (2013.01); *A61B 2017/003* (2013.01); *A61B 2017/00367* (2013.01); *A61B 2017/2905* (2013.01); *A61B 2017/2927* (2013.01); *A61B 2018/00178* (2013.01);
(Continued)

(58) Field of Classification Search
CPC ............ A61B 18/1492; A61B 18/1445; A61B 18/1442; A61B 18/1477; A61B 18/14; A61B 18/1482; A61B 18/082; A61B 2018/00577; A61B 2018/0212; A61B 2018/1465; A61B 2018/1425; A61B 2018/0091; A61B 2018/1412; A61B 2018/00601; A61B 2018/00184; A61B 2018/00178; A61B 2018/00202; A61B 2017/003; A61B 2017/00367;
(Continued)

(56) References Cited

U.S. PATENT DOCUMENTS

5,192,280 A * 3/1993 Parins ................ A61B 18/1485
606/48
6,309,388 B1 * 10/2001 Fowler ............... A61B 18/1485
600/564
(Continued)

*Primary Examiner* — Michael Peffley
(74) *Attorney, Agent, or Firm* — WPAT, PC (57) ABSTRACT

A steerable electrosurgical electrode is provided. The steerable electrosurgical electrode comprises a handle, a control element, a first tube, a second tube, a third tube, an electrode and an electrical transmission unit. The handle has a flat area therein, the control element has a plurality of positioning planes and pivotally connects to the handle such that one of the positioning planes rotatably abuts against the flat area, the first tube is positioned inside the second tube and pivotally connected to the control element, the third tube is connected to the second and the first tubes through a first and a second links, respectively, and the electrode is configured at the right end of the third tube. A user may manipulate the control element such that it abuts against the flat area at different positioning planes, to move the first tube inside the second tube, which in turns rotates the third tube and the electrode.

9 Claims, 6 Drawing Sheets (51) Int. Cl.
*A61B 17/29* (2006.01)
*A61B 18/00* (2006.01)

(52) U.S. Cl.
CPC ............ *A61B 2018/00184* (2013.01); *A61B 2018/00202* (2013.01); *A61B 2018/1425* (2013.01)

(58) Field of Classification Search
CPC .... A61B 2017/2905; A61B 2017/2927; A61B 2017/00309
See application file for complete search history.

(56) References Cited

U.S. PATENT DOCUMENTS

| | | | | |
|---|---|---|---|---|
| 6,451,014 | B1* | 9/2002 | Wakikaido | A61B 18/14 606/33 |
| 2003/0097128 | A1* | 5/2003 | Hayzelden | A61B 18/1492 606/41 |
| 2003/0109778 | A1* | 6/2003 | Rashidi | A61B 18/1492 600/374 |

* cited by examiner

STEERABLE ELECTROSURGICAL ELECTRODE

FIELD OF THE INVENTION

The present invention relates to an electrosurgical electrode, and more particularly to a steerable electrosurgical electrode.

BACKGROUND OF THE INVENTION

Conventional electrosurgical electrodes generally fall into two categories: the "straight type" having a straight main body, and the "pre-bending type" having a bent main body at a certain angle. However, surgeons always have problems using a conventional electrosurgical electrode in minimally invasive surgery due to limited surgical space. The straight type electrosurgical electrode is difficult to manipulate its tip electrode to a desired site in limited space. Although the pre-bending type has a fixed angle and may help to solve the problem, but only limited to a certain situation. Therefore, surgeons may have to prepare several pre-bending electrosurgical electrodes with various angles to deal with all potential situations they may encountered during surgery.

U.S. Pat. No. 7,105,003 discloses a surgical instrument for the removal of tissue, which has a gooseneck tube structure. The gooseneck tube structure makes the surgical instrument steerable, however it has a large turning radius with relatively poor rigidity In view of the foregoing, there is still a need for an improved electrosurgical electrode which is steerable, suitable for minimally invasive surgery, and has a relatively high rigidity.

SUMMARY OF THE INVENTION

Accordingly, the present invention provides a steerable electrosurgical electrode. The steerable electrosurgical electrode comprises a handle, a control element, a first tube, a second tube, a third tube, an electrode, and an electrical transmission unit.

The handle has a first left end, a first right end, an exterior surface, an interior surface, an accommodating space, and an opening. The interior surface comprises a flat area.

The control element has a control end and a positioning end. The positioning end is disposed in the accommodating space and comprises a plurality of positioning planes. The control end protrudes out of the opening. Further, the control element is pivoted to the handle by a first pin, such that the control element rotatably abuts against the flat area on one of the positioning planes.

The first tube has a second left end and a second right end. The second left end is pivoted to the control element by a second pin. The second right end extends away from the first left end of the handle.

The second tube is disposed around the first tube. The second tube has a third left end and third right end, wherein the third left end is connected to the first right end of the handle, and the third right end extends away from the first left end of the handle.

The third tube has a fourth left end and a fourth right end. The third tube is disposed to the right of the first and second tubes, such that the fourth left end is adjacent to the second right end of the first tube and the third right end of the second tube.

The electrode is disposed at the fourth right end of the third tube.

The electrical transmission unit comprises a power connector and an electrical wire. The electrical wire passes through the accommodating space and the interiors of the first and third tubes to electrically connect to the electrode.

In one embodiment of the present invention, the control element has a plurality of locking holes formed thereon, corresponding to the plurality of positioning planes.

In one embodiment of the present invention, the steerable electrosurgical electrode further comprises a locking member. The locking member is configured on the handle and includes a locking pin adapted to be operably received in one of the plurality of the locking holes. The locking pin is used to restrict the rotation of the control element.

In one embodiment of the present invention, the positioning end of the control element comprises two or more positioning planes.

In another embodiment of the present invention, the positioning end of the control element comprises three or more positioning planes.

In a further embodiment of the present invention, the positioning end of the control element comprises four or more positioning planes.

In a still further embodiment of the present invention, the positioning end of the control element comprises five or more positioning planes.

BRIEF DESCRIPTION OF THE DRAWINGS

The foregoing summary, as well as the following detailed description of the invention, will be better understood when read in conjunction with the appended drawing. In the drawings.

DESCRIPTION OF THE INVENTION

Unless defined otherwise, all technical and scientific terms used herein have the same meaning as commonly understood by a person skilled in the art to which this invention belongs.

As used herein, the singular forms "a", "an", and "the" include plural referents unless the context clearly dictates otherwise. Thus, for example, reference to "a sample" includes a plurality of such samples and equivalents thereof known to those skilled in the art.

Figure 1:
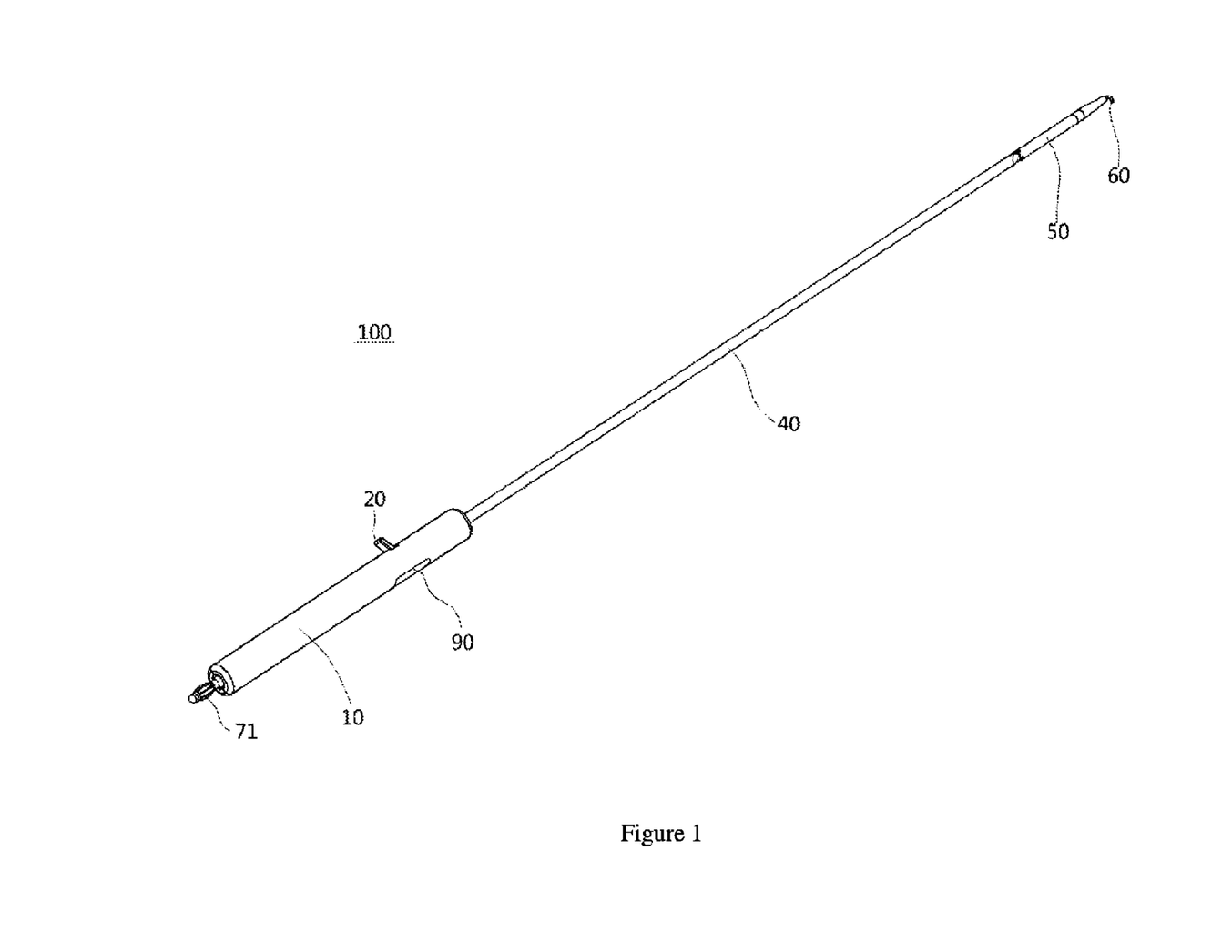
FIG. 1 is a perspective view of a steerable electrosurgical electrode in accordance with one embodiment of the present invention.
Figure 2:
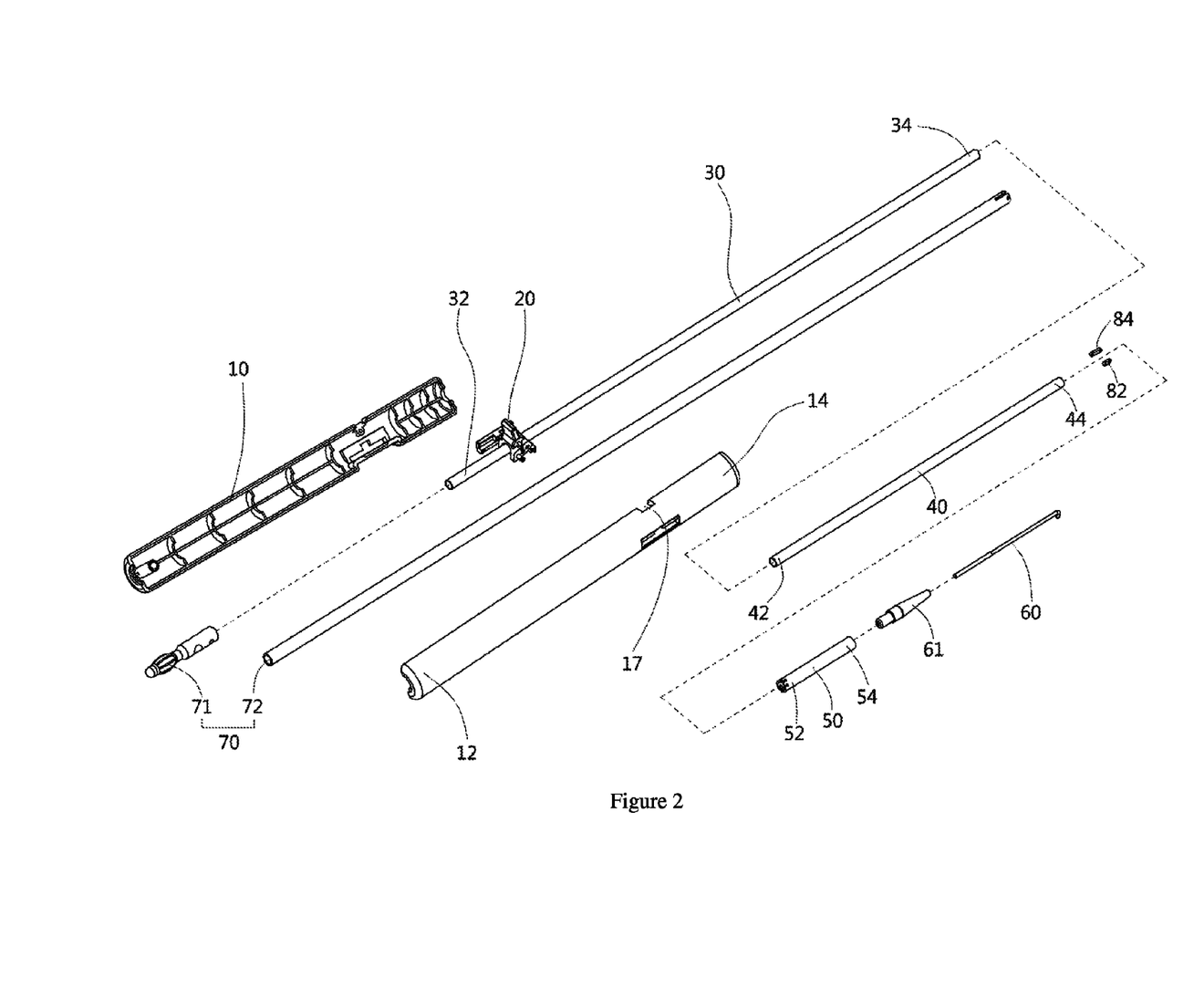
FIG. 2 is an exploded view of the steerable electrosurgical electrode in accordance with said embodiment of the present invention.
Figure 3:
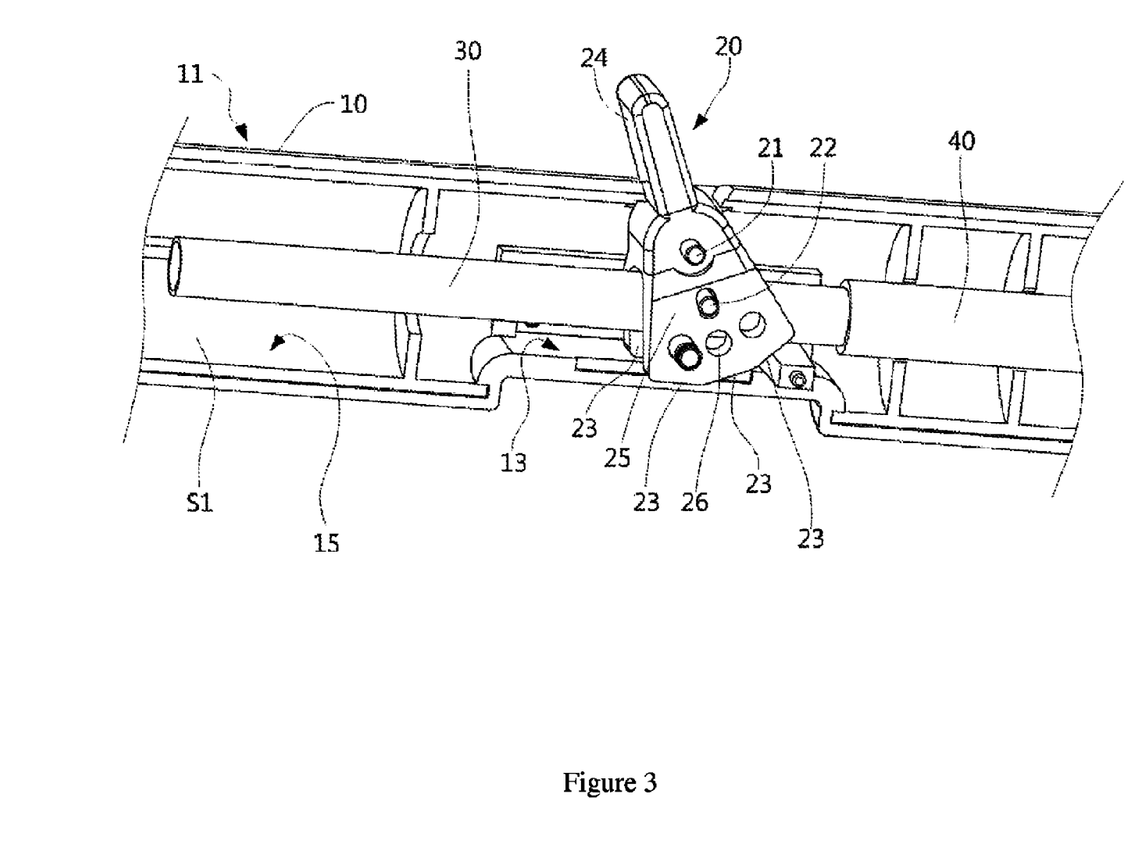
FIG. 3 is a perspective view illustrating the control element of the steerable electrosurgical electrode in accordance with said embodiment of the present invention.

Referring to FIGS. 1-3, shown is a steerable electrosurgical electrode 100 according to the present invention. The steerable electrosurgical electrode 100 comprises a handle 10, a control element 20, a first tube 30, a second tube 40, a third tube 50, an electrode 60, and an electrical transmission unit 70.

The handle 10 has a first left end 12, a first right end 14, an exterior surface 11, an interior surface 15, an accommodating space S1, and an opening 17, wherein the interior surface 11 comprises a flat area 13. The handle 10 may have a cylindrical housing structure, but is not limited thereto.

The control element 20 has a control end 24 and a positioning end 26, the positioning end 26 being disposed in the accommodating space S1 of the handle 10. The positioning end 26 has a plurality of positioning planes 23. On the other hand, the control end 24 protrudes out of the opening 17 of the handle 10. The control element 20 is pivoted to the handle 10 by a first pin 21, such that the control element 20 rotatably abuts against the flat area 13 inside the handle 10 on one of the positioning planes 23. In other words, the control element 20 is rotatable with respect to the first pin 21 when a force is applied to the control end 24, allowing the control element 20 to abut against the flat area 13 on its different positioning planes 23.

The first tube 30 has a second left end 32 and a second right end 34. The second left end 32 is pivoted to the control element 20 by a second pin 22. In addition, the second right end 34 extends away from the first left end 12 of the handle 10.

The second tube 40 has a third left end 42 and third right end 44 and is disposed around the first tube 30. Put differently, the first tube 30 is accommodated inside the second tube 40. The third left end 42 of the second tube 40 is connected to the first right end 14 of the handle 10, while its third right end 44 extends away from the first left end 12 of the handle 10.

Furthermore, the third tube 50 has a fourth left end 52 and a fourth right end 54, and is disposed to the right of the first and second tubes 30 and 40, such that the fourth left end 52 is adjacent to the second right end 34 of the first tube 30 and the third right end 44 of the second tube 40.

The electrode 60 is configured at the fourth right end 54 of the third tube 50. The electrical transmission unit 70 includes a power connector 71 and an electrical wire 72. The electrical wire 72 runs through the accommodating space S1 and the interiors of the first and third tubes 30 and 40 to electrically connect to the electrode 60.

Figure 4:
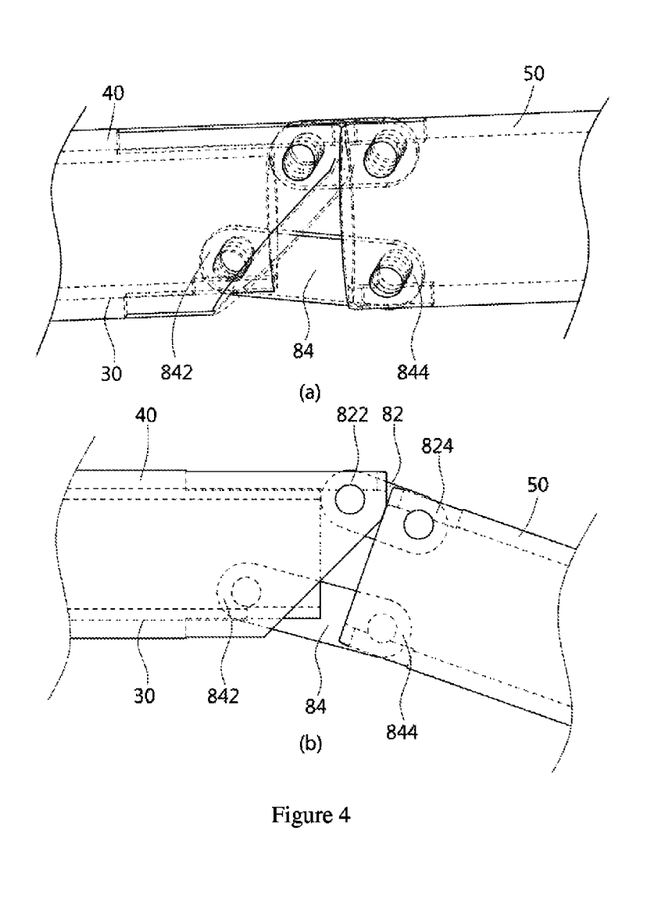
FIG. 4 is schematic view illustrating the first and second links of the steerable electrosurgical electrode in accordance with said embodiment of the present invention. (a) The third tube is in a default position. (b) The third tube is in an offset position.

Turning to FIG. 4, to embody the rotation of the third tube 50 with respect to a pivot point on the third right end 44 of the second tube 40, the steerable electrosurgical electrode 100 further comprises a first link 82 and a second link 84. The first link 82 has a fifth left end 822 and a fifth right end 824, and the second link 84 has a sixth left end 842 and a sixth right end 844. The fifth left end 822 of the first link 82 is pivoted to the third right end 44 of the second tube 40, while the fifth right end 824 of the first link 82 is pivoted to the fourth left end 52 of the third tube 50. On the other hand, the sixth left end 842 of the second link 84 is pivoted to the second right end 34 of the first tube 30, and the sixth right end 844 of the second link 84 is pivoted to the fourth left end 52 of the third tube 50 at a position different from that of the fifth right end 824 of the first link 82.

Accordingly, a user may manipulate the control element 20 through its control end 24, such that the control element 20 abuts against the flat area 13 of the interior surface 15 of the handle 10 on different positioning planes 23 of the control element 20, to move the first tube 30 forward or backward inside the second tube 40, which in turns moves the third tube 50 and the electrode 60. As a result, the third tube 50 disposed at a front end of the steerable electrosurgical electrode 100 and the electrode 60 configured therein front may be in a default position or be steerable to one or more different offset positions, corresponding to different positioning planes 23 in contact with the flat area 13. As shown in FIG. 4,(a), the third tube 50 may originally be in a default position, and when a user manipulates the control element 20 to move the first tube 30 backward (to the left of FIG. 4), the second link 84 is moved backward accordingly, causing the third tube 50 to rotate with respect to its pivot point on the second tube 40 (clockwise in FIG. 4; the first link 82 is also rotated clockwise) to an offset position as shown in FIG. 4,(b).

Figure 6:
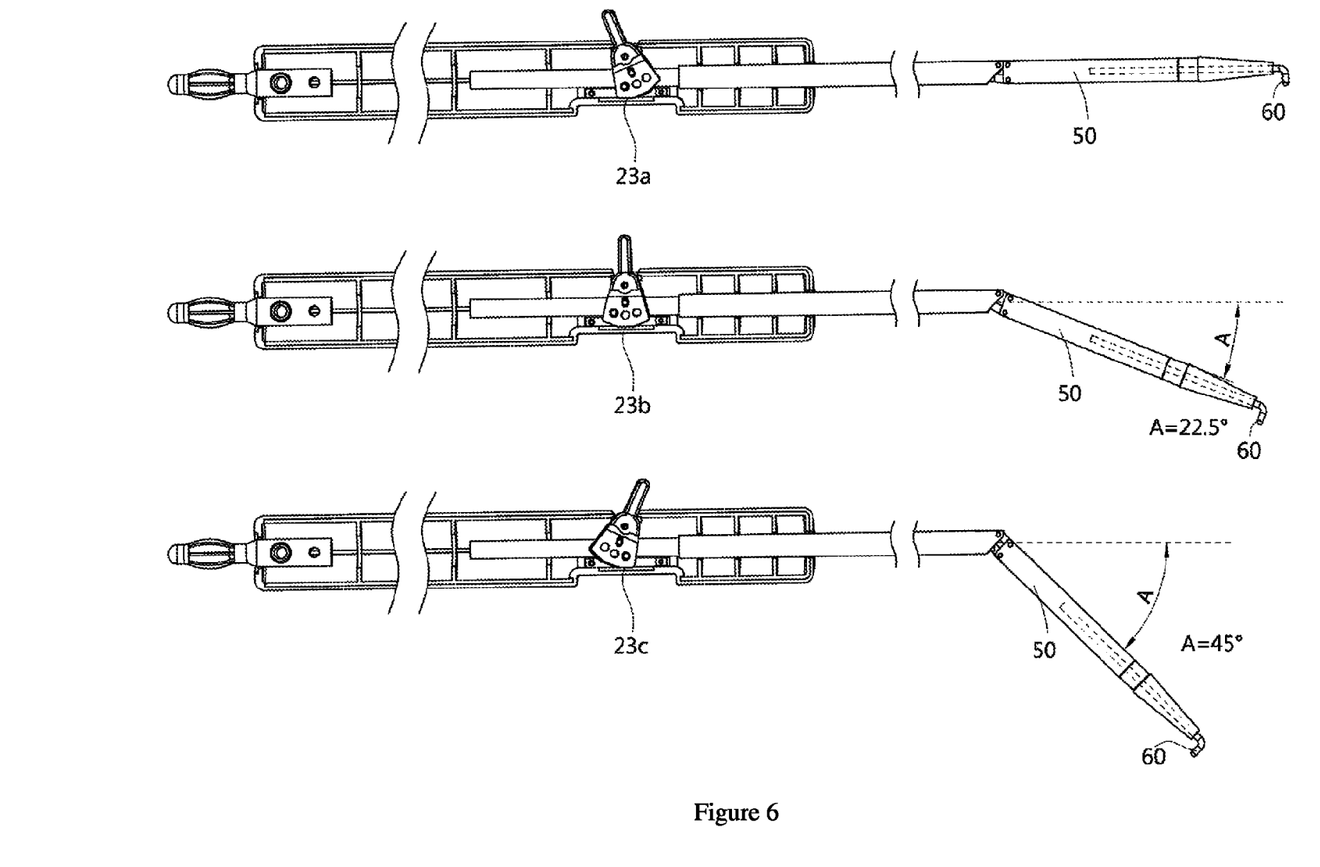
FIG. 6 shows schematic views of the steerable electrosurgical electrode in accordance with said embodiment of the present invention, with its electrode at different positions.

For example, as shown in FIGS. 3 and 6, in the case that the control element 20 has three positioning planes, i.e., a first positioning plane 23a, a second positioning plane 23b and a third positioning plane 23c, the third tube 50 along with the electrode 60 have three working positions, one default position and two offset positions, corresponding to the control element 20 being abutting against the flat area 13 on the first, second or third positioning plane 23a, 23b, 23c, respectively. Specifically, when the control element 20 abuts against the flat area 13 on the first positioning plane 23a, the third tube 50 and the electrode 60 are in the default position ("upright" position, as shown in the top of FIG. 6); when the control element 20 abuts against the flat area 13 on the second positioning plane 23b, the third tube 50 and the electrode 60 are in a first offset position (e.g., offset by an angle A of 22.5 degrees with respect to the default position, as shown in the middle of FIG. 6); and when the control element 20 abuts against the flat area 13 on the third positioning plane 23c, the third tube 50 and the electrode 60 are in a second offset position (e.g., offset by an angle A of 45 degrees with respect to the default position, as shown in the bottom of FIG. 6). Therefore, a user can freely switch the position of the third tube 50 and the electrode 60 between the default position, the first offset position and the second offset position through manipulating the control element 20. Further, a person of ordinary skill in the art can readily determine the number of the plurality of positioning planes and the offset angles according to practical demands. Preferably, the third tube 50 and the electrode 60 may have an offset angle ranging from −90 degrees to 90 degrees with respect to the upright default position.

According to certain embodiments of the present invention, the control element has two or more positioning planes, three or more positioning planes, four or more positioning planes, or five or more positioning planes.

Figure 5:
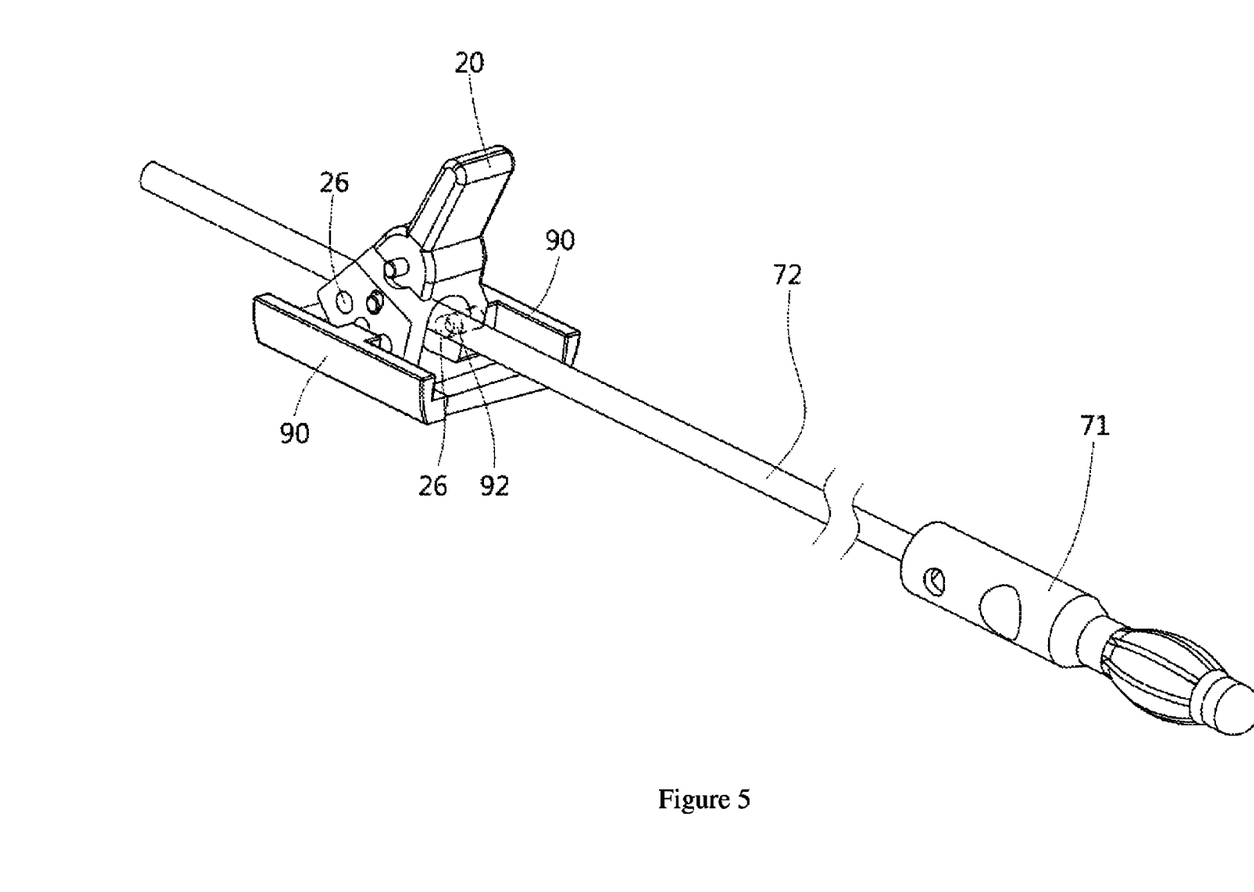
FIG. 5 is a perspective view illustrating the locking member of the steerable electrosurgical electrode in accordance with said embodiment of the present invention.

With reference to FIGS. 3 and 5, a plurality of locking holes 26 may be formed in the control element 20, corresponding to the plurality of positioning planes 23. In addition, referring to FIGS. 1-2 and 5, the steerable electrosurgical electrode may further comprises a locking member 90 configured on the handle 10. The locking member 90 includes a locking pin 92, which is adapted to be operably received in one of the plurality of the locking holes 26 to restrict the rotation of the control element 20 with respect to the first pin 21. Accordingly, after switching the third tube 50 and the electrode 60 to a desired position as described above, the user may lock the control element, the third tube 50 and the electrode 60 using the locking member 90, thus avoiding displacement of the third tube 50 and the electrode 60 during the operation.

It is believed that a person of ordinary knowledge in the art where the present invention belongs can utilize the present invention to its broadest scope based on the descriptions herein with no need of further illustration. Therefore, the descriptions and claims as provided should be understood as of demonstrative purpose instead of limitative in any way to the scope of the present invention.

We claim:

1. A steerable electrosurgical electrode, comprising:
   a handle having a first left end, a first right end, an exterior surface, an interior surface, an accommodating space, and an opening, the interior surface comprising a flat area;
   a control element having a control end and a positioning end, the positioning end being disposed in the accommodating space and comprising a plurality of positioning planes, and the control end protruding out of the opening, said control element pivoted to the handle by a first pin such that the control element rotatably abuts against the flat area on one of the positioning planes;
   a first tube having a second left end and a second right end, the second left end pivoted to the control element by a second pin, and the second right end extending away from the first left end of the handle;
   a second tube disposed around the first tube and having a third left end and third right end, the third left end connected to the first right end of the handle, and the third right end extending away from the first left end of the handle;
   a third tube having a fourth left end and a fourth right end, the third tube being disposed to the right of the first and second tubes such that the fourth left end is adjacent to the second right end of the first tube and the third right end of the second tube;
   an electrode disposed at the fourth right end of the third tube; and
   an electrical transmission unit comprising a power connector and an electrical wire, the electrical wire passing through the accommodating space and the interiors of the first and third tubes to electrically connect to the electrode.

2. The steerable electrosurgical electrode of claim 1, wherein the control element has a plurality of locking holes formed thereon corresponding to the plurality of positioning planes.

3. The steerable electrosurgical electrode of claim 2, further comprising a locking member configured on the handle, the locking member having a locking pin adapted to be operably received in one of the plurality of the locking holes to restrict the rotation of the control element.

4. The steerable electrosurgical electrode of claim 1, further comprising a first link having a fifth left end and a fifth right end, and a second link having a sixth left end and a sixth right end, wherein: the fifth left end of the first link is pivoted to the third right end of the second tube, and the fifth right end of the first link is pivoted to the fourth left end of the third tube; and the sixth left end of the second link is pivoted to the second right end of the first tube, and the sixth right end of the second link is pivoted to the fourth left end of the third tube.

5. The steerable electrosurgical electrode of claim 4, wherein the fifth right end of the first link and the sixth right end of the second link are pivoted to different positions of the fourth left end of the third tube.

6. The steerable electrosurgical electrode of claim 1, wherein the positioning end of the control element comprises two or more positioning planes.

7. The steerable electrosurgical electrode of claim 1, wherein the positioning end of the control element comprises three or more positioning planes.

8. The steerable electrosurgical electrode of claim 1, wherein the positioning end of the control element comprises four or more positioning planes.

9. The steerable electrosurgical electrode of claim 1, wherein the positioning end of the control element comprises five or more positioning planes.

* * * * *